United States Patent [19]

Nisato et al.

[11] Patent Number: 4,501,747
[45] Date of Patent: Feb. 26, 1985

[54] CERTAIN AMIDE DERIVATIVES OF 2-GUANIDINO-THIAZOLES AND COMPOSITIONS CONTAINING SAME

[75] Inventors: Dino Nisato, Pavia; Sergio Boveri, Monza, both of Italy; Romeo Roncucci, Paris, France; Paolo Carminati, Milan, Italy

[73] Assignee: Sanofi, Paris, France

[21] Appl. No.: 489,723

[22] Filed: Apr. 29, 1983

[30] Foreign Application Priority Data

May 10, 1982 [FR] France .................. 82 08097
Aug. 13, 1982 [FR] France .................. 82 14126

[51] Int. Cl.³ .................. C07D 411/12; C07D 263/28; A01N 31/455; A01N 31/42
[52] U.S. Cl. .................. 514/342; 546/280; 548/195; 544/336; 514/370
[58] Field of Search .................. 546/280, 316; 548/195; 424/266, 270

[56] References Cited

U.S. PATENT DOCUMENTS 3,743,647  7/1973  Naito et al. .................. 546/280

Primary Examiner—Alan L. Rotman

Attorney, Agent, or Firm—Weingarten, Schurgin, Gagnebin & Hayes

[57] ABSTRACT

Amides acting as histamine $H_2$ receptors antagonists, of formula

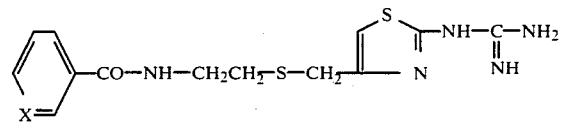

wherein X represents a N→O or C-NH-A-B group in which A is CO or $SO_2$ and B is alkyl, phenyl, pyridyl, pyridyl 1-oxide, pyrazinyl or thienyl; their salts; process for their preparation by reacting 2-(2-guanidinothiazol-4-ylmethylthio)ethylamine with a derivative of formula

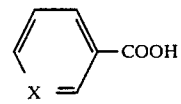

and optional salification; and pharmaceutical compositions containing same.

8 Claims, No Drawings

CERTAIN AMIDE DERIVATIVES OF 2-GUANIDINO-THIAZOLES AND COMPOSITIONS CONTAINING SAME

The present invention relates to amides having a histamine H receptor blocking activity, to their salts, to a process for their preparation and to pharmaceutical compositions containing them as active ingredients.

After the subdivision of histamine receptors into $H_1$ receptors (Ash and Schild, Brit. J. Pharmac. Chemother. 1966, 27, 427) and $H_2$ receptors (Black et al., Nature 1972, 236, 385) and the discovery that the selective block of the $H_2$ receptors induces an inhibition of the gastric secretion, many products have been proposed as antagonists of the histamine $H_2$ receptors, hereinafter referred to as "$H_2$-blockers". Thus, the compounds having received the International Non-proprietary Names burimamide, metiamide, cimetidine, ranitidine, tiotidine, etintidine, oxmetidine have formed the subject matter of a large number of scientific publications.

All of the above-mentioned products are characterised by the presence in their molecule of the following structure:

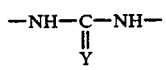
I wherein Y represents an oxygen or sulfur atom or an $N-CN$ or $CH-NO_2$ group, said structure being linear or included in a cycle as in the case of oxmetidine. The above-mentioned products are therefore all characterised by the presence of two geminal nitrogen atoms on a carbon atom.

Cimetidine, 2-cyano-1-methyl-3-[2-[[(5-methylimidazol-4-yl)methyl]thio]ethyl]guanidine having the structure I where Y is N—CN and ranitidine, N-[2-[[5-[(dimethylamino)methyl]furfuryl]thio]ethyl]-N'-methyl-2-nitro-1,1-ethenediamine, having the structure I where Y is CH—NO$_2$ are already utilized in therapy for the treatment of the gastric and duodenal ulcer.

Belgian Pat. No. 888 602 describes and claims amides of formula

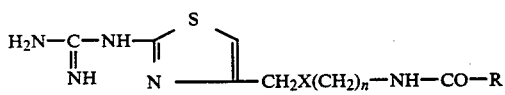
II wherein n represents an integer of from 2 to 4, R represents hydrogen, an alkyl group of from 1 to 6 carbon atoms (optionally substituted by a hydroxy, cyano, amino or phenoxy radical), a cycloalkyl radical of from 3 to 6 carbon atoms, an alkenyl radical of from 2 to 6 carbon atoms (optionally substituted by a phenyl or alkoxycarbonyl radical of from 2 to 7 carbons atoms) an alkadienyl radical of from 4 to 7 carbon atoms, an aryl radical of from 6 to 12 carbon atoms (optionally substituted by 1 to 3 substituents selected from the group consisting of halogen atoms and cyano, nitro, amino, dialkylamino radicals of from 2 to 10 carbon atoms, tetrazolyl, hydroxy, alkoxy of from 1 to 6 carbon atoms, benzoyloxy, alkoxycarbonyl of from 2 to 7 carbon atoms, sulfamoyl, alkylsulfonyl of from 1 to 6 carbon atoms, alkanesulfonamido of from 1 to 6 carbon atoms and alkanoyl of from 1 to 6 carbon atoms), or a pentagonal or hexagonal heterocycle (optionally substituted by a halogen atom or an alkyl of from 1 to 6 carbon atoms or phenyl radical) and X represents a simple bond or a thia radical as well as their pharmaceutically acceptables addition salts that are useful agents against the peptic ulcer or useful antagonists of the histamine $H_2$ receptors.

Among the compounds described in the above-mentioned patent, the compound of formula II where R=hydrogen, n=2 and X=thio, namely the 2-guanidino-4-[(2-formamido)ethylthiomethyl]thiazol, as maleate, shows an ED50 of 0.25 mg/kg i.v. in the acid secretion inhibiting activity of the rat stomach (Ghosh et al., Brit. J. Pharmacol. 1959, 13, 54).

The above Belgian patent more particularly includes compounds of formula II above where R is a pyridyl group or a phenyl group substituted by an alkanesulfonamido group of from 1 to 6 carbon atoms and specifically describes the compound wherein R is 3-pyridyl or a p—$CH_3$—$SO_2$—$NH$—$C_6H_4$— group.

It has now been found that a nicotinamide 1-oxide not having the structure I hereinabove has a good action antagonising the histamine $H_2$ receptors.

It has also been found that novel amidobenzamides possess an action antagonising the histamine $H_2$ receptors superior to that of analogous compounds described in Belgian Pat. No. 888 602.

It has further surprisingly found that the $H_2$ blocking action occurs at a satisfactory level only when the "amido" group is in the meta position of the benzamide phenyl ring.

Thus, the present invention provides, according to one of its aspects, amides of formula

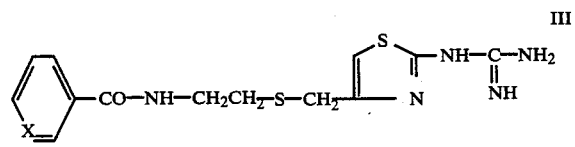
III wherein X represents a N→O or C—NH—A—B group, in which A represents a CO or SO$_2$ group and B represents an alkyl group of from 1 to 6 carbon atoms or a phenyl, pyridyl, pyridyl 1-oxide, pyrazinyl or thienyl group, as well as their pharmaceutically acceptable salts.

The pharmaceutically acceptable salts include the non-toxic salts derived from mineral or organic acids salifying one or the two basic functions present in the molecule of the compounds of formula III, such as hydrochloride, hydrobromide, sulfate, succinate, tartrate, citrate, fumarate, maleate, 4,4'-methylene-bis-(3-hydroxy-2-naphtoate), hereinafter referred to as "pamoate", 2-naphtalene-sulfonate, hereinafter referred to as "napsylate", methanesulfonate, hereinafter referred to as "mesylate", p-toluenesulfonate, hereinafter referred to as "tosylate", and the like.

According to another of its aspects, the present invention provides a process for the preparation of compounds of formula III above, said process comprising treating the 2-(2-guanidinothiazol-4-ylmethylthio)ethylamine of formula

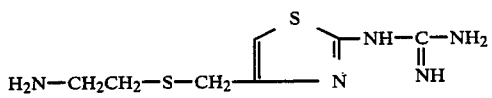

with a functional derivative of an acid of formula

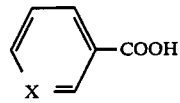

wherein X is as hereinabove defined, in an organic solvent at a temperature between 0° C. and the boiling temperature of the employed solvent and optionally converting the compound thus obtained into its pharmaceutically acceptable salts.

The activated free acid, the anhydride, a mixed anhydride, the chloride or an active ester may be used as a suitable functional derivative.

A preferred functional derivative of the acid of formula V above is represented by the following formula

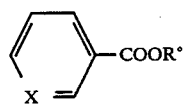

wherein X is as hereinabove defined and R° represents a nitrophenyl, methoxyphenyl, trityl or benzhydryl group.

The compounds of formula VI above are known in the literature or they can be easily prepared by reacting the acid V with the appropriate alcohol or phenol in the presence of a condensation agent such as dicyclohexylcarbodiimide in a solvent such as methylene chloride.

The reaction temperature may vary between 0° C. and the boiling point of the solvent employed, but the operation is generally carried out at room temperature or at 30°–50° C. It may be preferable to carry out the reaction in the cold when it is exothermic, as in the case of the chloride being used as a functional derivative of the acid of formula V.

An alcohol, such as methanol, or a halogenated solvent, such as methylene chloride, dichloroethane, chloroform and the like, is preferably used as a reaction solvent, but other organic solvents compatible with the reagents employed, for example acetonitrile, dioxane, tetrahydrofuran or a hydrocarbon such as hexane may also be used.

The reaction may be carried out in the presence of a proton acceptor, for example an alkaline carbonate or a tertiary amine, when hydrochloric acid, or another acid, forms during the reaction, but this proton acceptor is not indispensable for obtaining the final product.

The reaction is fairly rapid; after 2–4 hours at room temperature or at 30°–50° C. the reaction is generally over and the amide of formula III obtained is isolated according to conventional techniques in the form of free base or of one of its salts.

The free base may be converted into one of its pharmaceutically acceptables salts by treatment with a solution of the suitable acid in an organic solvent. If the amide III is isolated as a salt, the corresponding free base can be splitted off with an alcaline hydroxide or carbonate.

The novel compounds of formula III of the present invention, as well as their pharmaceutically acceptables salts, act as selective antagonists of the histamine $H_2$ receptors by selectively inhibiting the gastric secretion and are therefore useful for the treatment of the ulcerous disease.

The selective activity of the products of the present invention towards the receptors of type $H_2$ is confirmed by the absence of activity of type $H_1$ in the test of the contraction induced by histamine on the isolated guinea pig ileum.

The antagonistic activity of the amides of the present invention towards the histamine $H_2$ receptors was confirmed in the test of the antisecretory activity based on the antagonism for the hypersecretion induced by histamine in the atropinized rat, according to the method of Ghosh and Schild (Brit. J. Pharmacol. 1958, 13, 54), modified according to Black et al. (Nature 1972, 236, 385). According to this test, a gastric acid hypersecretion is induced by intravenous infusion of a sub-maximal dose of histamine equivalent to 15 mcmol/kg/hour and the gastric secretion is measured by perfusion of a physiological solution at a constant speed in the stomach of the animal.

Table I shows, for the three representative compounds of the present invention described, respectively, in the Examples 3, 4 and 1 hereinbelow, and herein indicated by their code numbers SR 57938 A, SR 57963 A and SR 57957 A and for four reference compounds, the 2-cyano-1-methyl-3-[2-[[(5-methylimidazol-4-yl)methyl]thio]ethyl]guanidine, hereinafter designated by its International Non-proprietary Name "cimetidine", the N-[2-[[5-[(dimethylamino)methyl]furfuryl]thio]ethyl]-N'-methyl-2-nitro-1,1-ethenediamine, hereinafter designated by its International Non-proprietary Name "ranitidine" and, respectively, the 4-methanesulfonamido-N-[2-(2-guanidinothiazol-4-ylmethylthio)ethyl]benzamide and N-[2-(2-guanidinothiazol-4-ylmethylthio)ethyl]nicotinamide, described in the above-mentioned Belgian Pat. No. 888 602 hereinafter designated "Compound A" and "Compound B", the dose (in mcmol/kg by intravenous route in a single administration) which inhibits by 50% the gastric hypersecretion induced by histamine (ID50). Such a ID50 represents the index of the gastric $H_2$-blocking action.

TABLE I

| Compound | DI50 (mcmol/kg) | Relative potency (cimetidine = 1) |
|---|---|---|
| Cimetidine | 0.95 | 1.00 |
| Ranitidine | 0.25 | 3.80 |
| Compound A | 1.66 | 0.57 |
| Compound B | 0.28 | 7.39 |
| SR 57938 A | 0.15 | 6.33 |
| SR 57963 A | 0.065 | 14.6 |
| SR 57957 A | 0.10 | 9.5 |

It results from this table that all the representative compounds of the present invention are more active than the reference compounds; more particularly the representative compounds are much more active than Compound A. This finding is very surprising considering that the chemical difference between SR 57938 A and "Compound A" is given by a mere position isomerism and that SR 57938 A is ten times more active than "Compound A".

With respect of their degree of activity, the compounds of the present invention are poorly toxic. For example, at a dose of 375 mg/kg by intraperitoneal route in the mouse, SR 57957 A does not cause any mortality. Its LD50 is higher than 900 mcmol/kg, whereas, under the same conditions, "Compounds B" shows a LD50 of 342 mcmol/kg.

Thus, the present invention, according to another of its aspects, provides pharmaceutical compositions containing, as active ingredients, the amides of formula III above, or their pharmaceutically acceptable addition salts.

The pharmaceutical compositions with $H_2$-blocking action according to the present invention may be formulated for oral, sublingual, sub-cutaneous, intramuscular, intravenous, transdermic or rectal administration, by mixing the active ingredients with conventional pharmaceutical carriers. They may be administered, in dosage unit forms, to animals and human beings for the treatment of gastric hypersecretion and peptic ulcers.

In order to obtain the desired $H_2$-blocking effect, the daily dose of active ingredient may vary between 1 and 100 mg per kg of body weight, preferably from 10 to 50 mg/kg.

Each unit dose may contain from 10 to 1000 mg, preferably from 100 to 500 mg, of active ingredient in combination with a pharmaceutical carrier. This unit dose may be administered 1 to 4 times daily.

The appropriate unit forms of administration comprise tablets, capsules, powders, granules and oral solutions or suspensions and the forms for sublingual administration, suppositories as well as the vials for parenteral administration.

When a solid composition is prepared in the form of tablets, the main active ingredient is mixed with a pharmaceutical excipient such as gelatine, starch, lactose, magnesium stearate, talc, arabic gum and the like.

The tablets may be coated with sucrose or other appropriate materials or they may be treated so that their activity is extended or delayed and that they continually release a predetermined amount of active ingredient.

A preparation in capsules is obtained by mixing the active ingredient with a diluent and by pouring the mixture obtained in soft or hard capsules.

A preparation in the form of syrup or elixir may contain the active ingredient jointly with a sweetening agent, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents as well.

For rectal applications, suppositories are prepared with binding agents melting at rectal temperature, for example, cocoa butter or polyethyleneglycols.

For oral administration in drops or for parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules, possibly with one or more supports or additives.

The following examples illustrate the invention without, however, limiting its scope.

EXAMPLE 1

To a solution of 6.1 g of 2-(2-guanidinothiazol-4-ylmethylthio)ethylamine hydrochloride and 30 ml of triethylamine in 100 ml of methanol, 5 g of the hydrochloride of nicotinoyl chloride 1-oxide are added portionwise under stirring at a temperature of $-30°$ C. The mixture is stirred at first for 15 minutes at $-30°$ C. and afterwards 1 hour at room temperature, then it is filtered and the solvent evaporated under reduced pressure. The residue is taken up with 20 ml of water and the solution so obtained is treated with a concentrated sodium hydroxide solution. The product is extrated with ethyl acetate containing 10% of ethanol, the solvent is evaporated and the crude oil is purified by chromatography on $SiO_2$ by using a methanol:chloroform 1:4 mixture as an eluent. Thus, 3.8 g of N-[2-(2-guanidinothiazol-4-ylmethylthio)ethyl]-3 pyridinecarboxamide-1 oxide (SR 57957) are obtained as a pale-yellow oil.

$^1$H NMR-Solvent: DMSO-$d_6$. $S_{TMS}$ (ppm): 2.68(2H, m→t); 3.44 (2H, m→q); 3.63(2H, s); 6.48(1H, s); 6.83(sb); 7.46(1H, dd, $J_1=6$ Hz, $J_2=8$ Hz); 7.68(1H, ddd, $J_1=8$ Hz, $J_2\simeq J_3\simeq 2$ Hz); 8.30(1H, ddd, $J_1=6$ Hz, $J_2\simeq J_3\simeq 2$ Hz); 8.53(1H, dd, $J_1\simeq J_2\simeq 2$ Hz); 8.83(1H, tb). The signals at 8.83 ppm and 6.83 ppm disappear after addition of $D_2O$.

To a solution of the product thus obtained in 25 ml of 95% ethanol there is added 30 ml of fumaric acid dissolved in 30 ml of 95% ethanol. The precipitate is crystallized from 30 ml of water to yield 2.6 g of the neutral fumarate of N-[2-(2-guanidinothiazol-4-ylmethylthio)ethyl]-3-pyridine carboxamide 1-oxide (SR 57957 A); m.p. 220°–222° C. (dec.).

EXAMPLE 2

To a solution of 2.2 g of the neutral fumarate of N-[2-(2-guanidinothiazol-4-ylmethylthio)ethyl]-3-pyridinecarboxamide 1-oxide in 15 ml of water there is added sodium hydroxide until to a distinctly basic reaction. The product is extrated with ethyl acetate containing 10% ethanol; the organic phase is dried on anhydrous sodium sulfate and evaporated to dryness. Thus, 1.7 g of a viscous liquid which crystallizes slowly and solidifies as an amorphous solid are obtained. The structure of the N-[2-(2-guanidinothiazol-4-ylmethylthio)ethyl]-3-pyridinecarboxamide 1-oxide thus obtained has been confirmed by NMR and IR.

EXAMPLE 3

A solution of 0.015 mol of 2-(2-guanidinothiazol-4-ylmethylthio)ethylamine, 0.015 mol of 4-nitrophenyl 3-methanesulfonamidobenzoate (m.p. 162°–164° C., prepared from 3-methanesulfonamidobenzoic acid and 4-nitrophenol in methylene chloride in the presence of dicyclohexylcarbodiimide) and 0.035 mol of triethylamine in 150 ml of methanol is heated at 40° C. under stirring for 4 hours. Then the solvent is evaporated under reduced pressure and the residue is taken up with 20 ml of water and 100 ml of ethyl acetate. The organic phase is dried on anhydrous sodium sulfate, the solvent is evaporated under reduced pressure and the residue is dissolved in 50 ml of warm ethyl acetate. The solution is filtered and the filtrate is acidified with hydrogen chloride in isopropanol. Thus, 3-methanesulfonamido-N-[2-(2-guanidinothiazol-4-ylmethylthio)ethyl]benzamide hydrochloride is obtained, which, after crystallization from 20 ml of water gives 2 g of the monohydrate, SR 57938 A; m.p. 117°–120° C.

EXAMPLE 4

A mixture of 5.5 g of 2-(2-guanidinothiazol-4-ylmethylthio)ethylamine dihydrochloride, 3.65 g of triethylamine and 3.7 g of 4-nitrophenyl 3-benzenesulfonamidobenzoate (m.p. 175°–178° C., prepared from 3-benzenesulfonamidobenzoic acid and 4-nitrophenol in methylene chloride in the presence of dicyclohexylcarbodiimide) is stirred at the temperature of 40° C. for 90 minutes, then it is evaporated under reduced pressure to dryness. The residue is taken up with 150 ml of ethyl acetate and washed twice with 10 ml of water. The solution is dried on anhydrous sodium sulfate, evaporated and the residue is chromatographied on silica with a chloroform:ethanol 4:1 mixture. Thus, 3.8 g of 3-benzenesulfonamido-N-[2-(2-guanidinothiazol-4-ylmethylthio)ethyl]benzamide are obtained as an oil which is dissolved in absolute ethanol and treated with fumaric acid in absolute ethanol. Thus, 3.6 g of crude product are obtained, which, after crystallization from 40 ml of 95% ethanol, gives 2.4 g of neutral fumarate of 3-benzenesulfonamido-N-[2-(2-guanidinothiazol-4-ylmethylthio)ethyl]benzamide, SR 57963 A, $C_{20}H_{22}N_6O_3S_4 \cdot \frac{1}{2}C_4H_4O_4$; m.p. 139°–141° C.

In the same manner, by reacting the 2-(2-guanidinothiazol-4-ylmethylthio)ethylamine dihydrochloride with, respectively, the 4-nitrophenyl 3-acetamidobenzoate and the 4-nitrophenyl 3-nicotinoylaminobenzoate, the 3-acetamido-N-[2-(2-guanidinothiazol-4-ylmethylthio)ethyl]benzamide neutral fumarate and
the 3-nicotinoylamino-N-[2-(2-guanidinothiazol-4-ylmethylthio)ethyl]benzamide neutral fumarate are obtained.

EXAMPLE 5

Tablets comprising one of the products described in Examples 1 to 4 having the following composition:
  active substance: 100 mg
  lactose: 70 mg
  potato starch: 40 mg
  polyvinylpyrrolidone: 8 mg
  magnesium stearate: 2 mg
The mixture of the active substance with the lactose and potato starch is moistened with a 15% alcohol solution of polyvinylpyrrolidone, the granules formed are passed through a 1 mm sieve, mixed with the magnesium stearate and tablets are formed by compression. Weight of a tablet: 220 mg.

EXAMPLE 6

The tablets manufactured as described in Example 5 are coated in known manner by a coating for pills consisting essentially of sugar and talc and the finished pills are polished with beeswax. Weight of a pill: 300 mg.

EXAMPLE 7

Capsules comprising one of the products described in Examples 1 to 4, having the following composition:
  active substance: 200 mg
  cornstarch: 90 mg
  talc: 10 mg
The active substance and the excipients are intimately mixed and the mixture thus obtained is introduced into gelatine capsules of dimension 1. Contents of a capsule: 300 mg.

EXAMPLE 8

Suppositories comprising one of the products described in Examples 1 to 4, having the following composition:
  active substance: 300 mg
  mass for suppositories (Witepsol W 45): 1,450 mg
The finely pulverized active substance is suspended in the mass for suppositories at 37° C. and the mixture is poured into moulds which are slightly cooled beforehand. Weight of a suppository: 1,750 mg.

EXAMPLE 9

Tablets comprising one of the products described in Examples 1 to 4, having the following composition:
  active substance: 150 mg
  microcrystalline cellulose: 75 mg
  lactose: 100 mg
  magnesium stearate: 7 mg
  talc: 18 mg
The powders are passed through a 0.3 mm sieve, then the ingredients are mixed until a homogeneous mixture is obtained which is compressed and granulated. The granules thus obtained are utilized to form tablets by compression. Weight of a tablet: 350 mg.

EXAMPLE 10

By operating as described in Example 9, tablets comprising one of the products described in Examples 1 to 4, having the following composition:
  active substance: 350 mg
  microcrystalline cellulose: 100 mg
  lactose: 125 mg
  magnesium stearate: 10 mg
  talc: 15 mg
are prepared. Weight of a tablet: 600 mg.

EXAMPLE 11

By operating as described in Example 7, gelules containing respectively 100 mg and 150 mg of SR 57957 A are prepared.

We claim:

1. An amide of formula

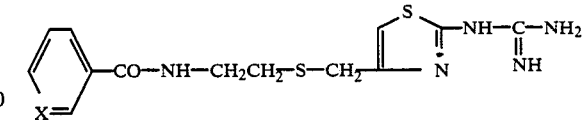

in which X represents a N→O or C-NH-A-B group, wherein A represents a CO or $SO_2$ group and B represents an alkyl group of from 1 to 6 carbon atoms or a phenyl group, or a pharmaceutically acceptable acid addition salt thereof.

2. The N-[2-(2-guanidinothiazol-4-ylmethylthio)ethyl]-3-pyridinecarboxamide 1-oxide or pharmaceutically acceptable acid addition salt thereof.

3. The N-[2-(2-guanidinothiazol-4-ylmethylthio)ethyl]-3-pyridinecarboxamide 1-oxide neutral fumarate.

4. The 3-methanesulfonamido-N-[2-(2-guanidinothiazol-4-ylmethylthio)ethyl]benzamide or a pharmaceutically acceptable acid addition salt thereof.

5. The 3-benzenesulfonamido-N-[2-(2-guanidinothiazol-4-ylmethylthio)ethyl]benzamide or a pharmaceutically acceptable acid addition salt thereof.

6. A pharmaceutical composition having histamine H₂ receptor antagonist action comprising an effective amount of a compound of claim 1, 2, 3, 4, or 5 as an active ingredient, in combination with an inert pharmaceutically acceptable carrier.

7. A pharmaceutical composition as claimed in claim 6 which is in dosage unit form comprising from 10 to 1000 mg of active ingredient in combination with an inert pharmaceutically acceptable carrier.

8. A pharmaceutical composition as claimed in claim 7 comprising from 100 to 500 mg of active ingredient per dosage unit.

* * * * *